United States Patent
Moss et al.

[11] Patent Number: 5,810,803
[45] Date of Patent: Sep. 22, 1998

[54] CONFORMAL POSITIONING ASSEMBLY FOR MICROWAVE ABLATION CATHETER

[75] Inventors: Jon F. Moss, Antioch; Peter Sturzu, Cupertino; Hiep P. H. Nguyen, Fremont, all of Calif.

[73] Assignee: Fidus Medical Technology Corporation, Fremont, Calif.

[21] Appl. No.: 732,045

[22] Filed: Oct. 16, 1996

[51] Int. Cl.[6] .............................. A61B 17/39; A61N 5/02
[52] U.S. Cl. .............................. 606/33; 606/41; 607/101; 607/156
[58] Field of Search ........................ 606/33, 41; 607/101, 607/102, 113, 122, 154, 156; 600/374

[56] References Cited

U.S. PATENT DOCUMENTS

| | | |
|---|---|---|
| 4,244,371 | 1/1981 | Farin . |
| 4,409,993 | 10/1983 | Furihata . |
| 4,416,276 | 11/1983 | Newton et al. . |
| 4,494,539 | 1/1985 | Zenitani . |
| 4,601,296 | 7/1986 | Yerushalmi . |
| 4,641,649 | 2/1987 | Walinsky et al. . |
| 4,657,015 | 4/1987 | Irnich . |
| 4,800,899 | 1/1989 | Elliott . |
| 4,825,880 | 5/1989 | Stauffer et al. . |
| 4,841,988 | 6/1989 | Fetter et al. . |
| 4,924,863 | 5/1990 | Sterzer . |
| 4,945,912 | 8/1990 | Langberg . |
| 5,019,076 | 5/1991 | Yamanashi et al. . |

(List continued on next page.)

FOREIGN PATENT DOCUMENTS

| | | |
|---|---|---|
| WO93/08757 | 5/1993 | WIPO . |
| WO93/20767 | 10/1993 | WIPO . |
| WO93/20768 | 10/1993 | WIPO . |
| WO93/20886 | 10/1993 | WIPO . |
| WO93/20893 | 10/1993 | WIPO . |
| WO 96/36397 | 11/1996 | WIPO . |

OTHER PUBLICATIONS

Landberg et al., "Catheter Ablation of the Atrioventricular Junction Using a Helical Microwave Antenna: A Novel Means of Coupling Energy to the Endocardium", vol. 14, Dec. 1991, pp. 2105–2113.

*Primary Examiner*—Lee Cohen
*Attorney, Agent, or Firm*—Beyer & Weaver, LLP

[57] ABSTRACT

An ablation catheter includes an elongated flexible tubular member adapted to be inserted into a vessel in the body of a patient. A transmission line is disposed within the tubular member and a transducer is coupled to the transmission line for generating an electric field sufficiently strong to cause tissue ablation. A shape memory wire is positioned at a distal portion of the catheter adjacent the transducer to facilitate straightening the catheter tip after use. In one preferred embodiment, the shape memory wire may be a flat wire which is formed from copper beryllium, a steel alloy, or nickel titanium. In another embodiment, the transmission line of the catheter is a coaxial cable, and the transducer is a helical antenna coil that is adapted to radiate electromagnetic energy in the microwave frequency range. In yet another embodiment, the shape memory wire is positioned within the antenna coil. Methods for manufacturing and using such ablation catheters are also described.

18 Claims, 7 Drawing Sheets

U.S. PATENT DOCUMENTS

| | | |
|---|---|---|
| 5,045,056 | 9/1991 | Behl . |
| 5,097,845 | 3/1992 | Fetter et al. . |
| 5,100,388 | 3/1992 | Behl et al. . |
| 5,129,396 | 7/1992 | Rosen et al. . |
| 5,150,717 | 9/1992 | Rosen et al. . |
| 5,172,699 | 12/1992 | Svenson et al. . |
| 5,188,122 | 2/1993 | Phipps et al. . |
| 5,190,054 | 3/1993 | Fetter et al. . |
| 5,230,349 | 7/1993 | Langberg . |
| 5,246,438 | 9/1993 | Langberg . |
| 5,300,068 | 4/1994 | Rosar et al. . |
| 5,300,099 | 4/1994 | Rudie . |
| 5,314,466 | 5/1994 | Stern et al. . |
| 5,363,861 | 11/1994 | Edwards et al. ........................ 607/122 |
| 5,364,336 | 11/1994 | Carr . |
| 5,364,392 | 11/1994 | Warner et al. . |
| 5,370,644 | 12/1994 | Langberg . |
| 5,370,677 | 12/1994 | Rudie et al. . |
| 5,383,922 | 1/1995 | Zipes et al. . |
| 5,405,346 | 4/1995 | Grundy et al. . |
| 5,487,757 | 1/1996 | Truckai et al. ........................ 607/122 |
| 5,500,012 | 3/1996 | Brucker et al. ........................ 607/122 |
| 5,578,007 | 11/1996 | Imran ....................... 606/41 |
| 5,643,255 | 7/1997 | Organ ....................... 606/41 |

CONFORMAL POSITIONING ASSEMBLY FOR MICROWAVE ABLATION CATHETER

BACKGROUND OF THE INVENTION

1. Field of Invention

The present invention relates generally to ablation catheter systems that use electromagnetic energy in the microwave frequencies to ablate internal bodily tissues. More particularly, an ablation catheter with a shape memory conformal positioning assembly and a method for manufacturing such an ablation catheter are disclosed.

2. Description of the Prior Art

Catheter ablation has recently become an important therapy for the treatment of cardiac arrhythmias, cardiac disrhythmias and tachycardia. Most approved ablation catheter systems now utilize radio frequency (RF) energy as the ablating energy source. However, RF energy has several limitations including the rapid dissipation of energy in surface tissues which results in shallow "burns" and a failure to access deeper arrhythmic tissues. As such, catheters which utilize electromagnetic energy in the microwave frequency range as the ablation energy source are currently being developed. Microwave frequency energy has long been recognized as an effective energy source for heating biological tissues and has seen use in such hyperthermia applications as cancer treatment and preheating of blood prior to infusions. Catheters which utilize microwave energy have been observed to be capable of generating substantially larger lesions than those generated by RF catheters, which greatly simplifies the actual ablation procedures. Some catheter systems which utilize microwave energy are described in the U.S. Pat. Nos. 4,641,649 to Walinsky; 5,246,438 to Langberg; 5,405,346 to Grundy, et al.; and 5,314,466 to Stern, et al, each of which is incorporated herein by reference.

Atrial fibrillation is one type of cardiac arrhythmia which may be treated using catheter ablation. Cardiac arrhythmias are generally circuits, known as "arrhythmia circuits," which form within the chambers of the heart. As is known to those skilled in the art, arrhythmia circuits are abnormal electrical connections which may form in various areas of the heart. For example, arrhythmia circuits may form around veins and/or arteries which lead away from and to the heart. Cardiac arrhythmias may occur in any area of the heart where arrhythmia circuits are formed.

Atrial fibrillation occurs in the atria of the heart, and more specifically at the region where pulmonary veins are located, atrial fibrillation may occur. In atrial fibrillation, arrhythmia circuits form within the atria and between pulmonary veins. Due to the fact that these arrhythmia circuits prevent the heart from beating normally, cutting the arrhythmia circuits is necessary to restore a normal heart beat. Many different cutting patterns may be implemented to cut arrhythmia circuits and, specifically, arrhythmia circuits formed within the atria.

Figure 1A:
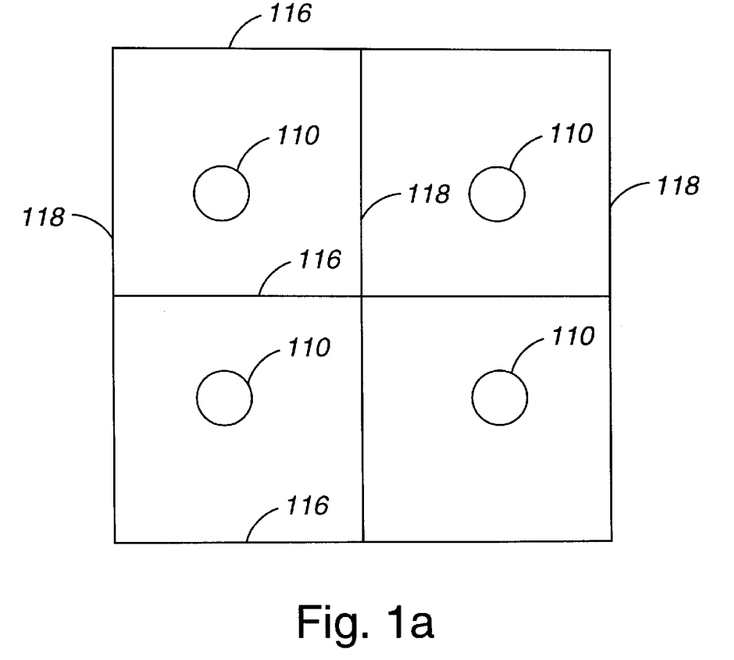
FIG. 1a is a diagrammatic illustration of one cutting pattern for circuits around pulmonary veins.

FIG. 1a is a diagrammatic illustration of one cutting pattern for arrhythmia circuits. This particular cutting pattern is well-suited for use in cutting arrhythmia circuits formed around pulmonary veins. That is, this cutting pattern may be used in atrial fibrillation applications. FIG. 1a shows cross-sections of pulmonary veins 110. It should be appreciated that the orientation of pulmonary veins 110 as shown is exaggerated for illustrative purposes. Arrhythmia circuits (not shown), or connections, may form between pulmonary veins 110. In order to eliminate the circuits, thereby eliminating unwanted, or abnormal, electrical connections in the heart, circuits between pulmonary veins 110 may be cut. As shown, cutting-lines 116, 118 may be formed between and around pulmonary veins 110 in order to cut circuits formed between pulmonary veins 110. These cutting-lines 116, 118 are essentially lesions which disrupt arrhythmia circuits formed within the atria of the heart. In the described embodiment, cutting-lines 116, 118 form linear lesions. In other embodiments, cutting-lines 116, 118 may not necessarily form linear lesions. Also, as shown, cutting-lines 116 are formed orthogonally to cutting-lines 118, although cutting-lines formed between and around pulmonary veins 110 may take on any suitable orientation.

Figure 1B:
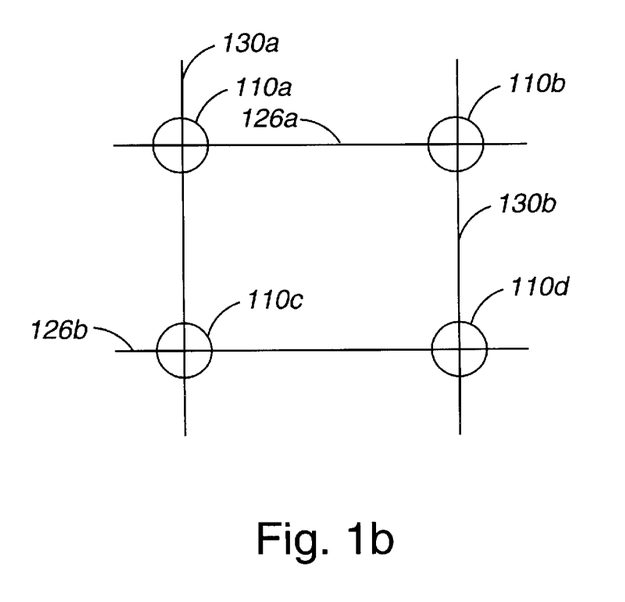
FIG. 1b is a diagrammatic illustration of another cutting pattern for circuits around pulmonary veins.

FIG. 1b is a diagrammatic illustration of a second cutting pattern for arrhythmia circuits. As shown, FIG. 1b illustrates a second cutting pattern which may be used to cut arrhythmia circuits formed around pulmonary veins for atrial fibrillation applications. Cross-sections of pulmonary veins 110 are shown with cutting-lines 126, 130 formed between adjacent pulmonary veins 110. By way of example, cutting-line, or lesion, 126a is formed between adjacent pulmonary veins 110a and 110b. Similarly, cutting-line 130a is formed between adjacent pulmonary veins 110a and 110c. As will be appreciated by those skilled in the art, although cutting-lines 126, 130 have been drawn "through" pulmonary veins 110, the pulmonary veins 110 are not actually cut through. Rather, the arrhythmia circuits (not shown) formed between pulmonary veins 110 are cut through.

The process of positioning a catheter in different locations within a heart chamber is often inefficient, as conventional catheters often must be removed and repositioned for each ablation process. For example, referring back to FIG. 1b, conventional ablation catheters are often completely removed from the atrium after cutting-line 130a is created in order to reposition the catheter to create cutting-line 130b. This is often necessary because the process of positioning the catheter in order to form cutting-line 130a often results in a bending of the catheter tip, or the portion of the catheter which contains an antenna, as the catheter tip conforms to the wall of the atrium. Once the catheter tip is bent, it becomes difficult to precisely position the tip, as the already bent tip must be conformed to another portion of the atrium. As such, the catheter tip must often be removed from a person's body in order to straighten the catheter tip. The process of constantly removing and reinserting a catheter into a person's body during an ablation procedure is inefficient, time-consuming, and painful. Therefore, it would be desirable to have a catheter tip which does not generally require the removal of the catheter tip from the human body for straightening purposes. That is, what is desired is a self-straightening catheter tip.

SUMMARY OF THE INVENTION

To achieve the foregoing and in accordance with the purpose of the present invention, a conformally positionable ablation catheter is disclosed. The ablation catheter includes an elongated flexible tubular member adapted to be inserted into a vessel in the body of a patient. A transmission line is disposed within the tubular member and a transducer is coupled to the transmission line for generating an electric field sufficiently strong to cause tissue ablation. A shape memory wire is positioned at a distal portion of the catheter adjacent the transducer to facilitate straightening the catheter tip after use. In one preferred embodiment, the shape memory wire may be a flat wire which is formed from a chromium alloy, a molybdenum alloy, or nickel titanium.

In another embodiment, the transmission line of the catheter is a co-axial cable, and the transducer is a helical antenna coil that is adapted to radiate electromagnetic energy in the microwave frequency range. In such an embodiment, the shape memory wire is positioned within the antenna coil.

A method for manufacturing a conformally positionable catheter involves attaching an antenna coil to a transmission line and inserting a shape memory metal through the antenna coil such that the shape memory metal extends longitudinally within the antenna coil. The antenna coil is then filled with a first dielectric material in a first molding operation. Positioning ribs, which are used to orient the filled antenna coil in a mold which is used to encapsulate the filled antenna coil with a second dielectric material, may be created with the first dielectric material such that the positioning ribs are aligned along the longitudinal axis of the antenna coil.

In one embodiment, the method for manufacturing a conformally positionable catheter further involves inserting sensor leads through the antenna coil along the longitudinal axis of the antenna coil and creating an extension plug at the distal end of the antenna coil using the first dielectric material. In such embodiments, sensors attached to the sensor leads are mounted over the extension plug.

A method for medical treatment using an ablation catheter system that includes a catheter tip with a transmission line, a transducer, and a shape memory wire which defines a neutral orientation for the catheter tip involves introducing the catheter into a patient's body such that a distal portion of the catheter is positioned in a cardiac chamber. Once the catheter is positioned, the tip portion of the catheter is substantially conformed to a wall of the chamber. Electromagnetic energy may then be applied to the transmission line to cause ablation of cardiac tissue. The catheter tip is repositioned and cardiac tissue is ablated as required. When the catheter tip is repositioned, the shape memory metal causes the catheter to return substantially to the neutral orientation. Partially withdrawing the catheter from the patient's body also causes the catheter to return substantially to the neutral orientation, while further introducing the catheter into the patient's body causes the catheter to further conform to the wall of the chamber.

The method for medical treatment may also include monitoring electro-physiological signals using catheter electrodes, determining an appropriate ablation position based at least in part on the monitored electro-physiological signals, and positioning the transducer at the determined appropriate ablation position. In one preferred embodiment, microwave energy is applied to the transmission line to cause the ablation.

BRIEF DESCRIPTION OF THE DRAWINGS

The invention, together with further advantages thereof, may best be understood by reference to the following description taken in conjunction with the accompanying drawings in which:

FIG. 2b is a diagrammatic cross-sectional view of the conformally positionable ablation catheter tip of FIG. 2a.

FIG. 5b is a diagrammatic longitudinal side view of the conformally positionable antenna assembly of FIG. 5a.

DETAILED DESCRIPTION OF THE DRAWINGS

A presently preferred conformally positionable microwave ablation catheter system in accordance with the present invention will be described below making reference to the accompanying drawings. A conformally positionable microwave ablation catheter system is capable of conforming to a surface, as for example a wall of a cardiac chamber. When the conformally positionable catheter system is either repositioned within the cardiac chamber, a shape memory wire positioned at a distal portion, i.e. catheter tip, of the catheter enables the catheter to reconform to the wall of the cardiac chamber without the need for removing the catheter tip from a patient's body for straightening. Similarly, when the catheter is withdrawn from the patient's body, the shape memory wire facilitates the straightening of the catheter tip.

Figure 2A:
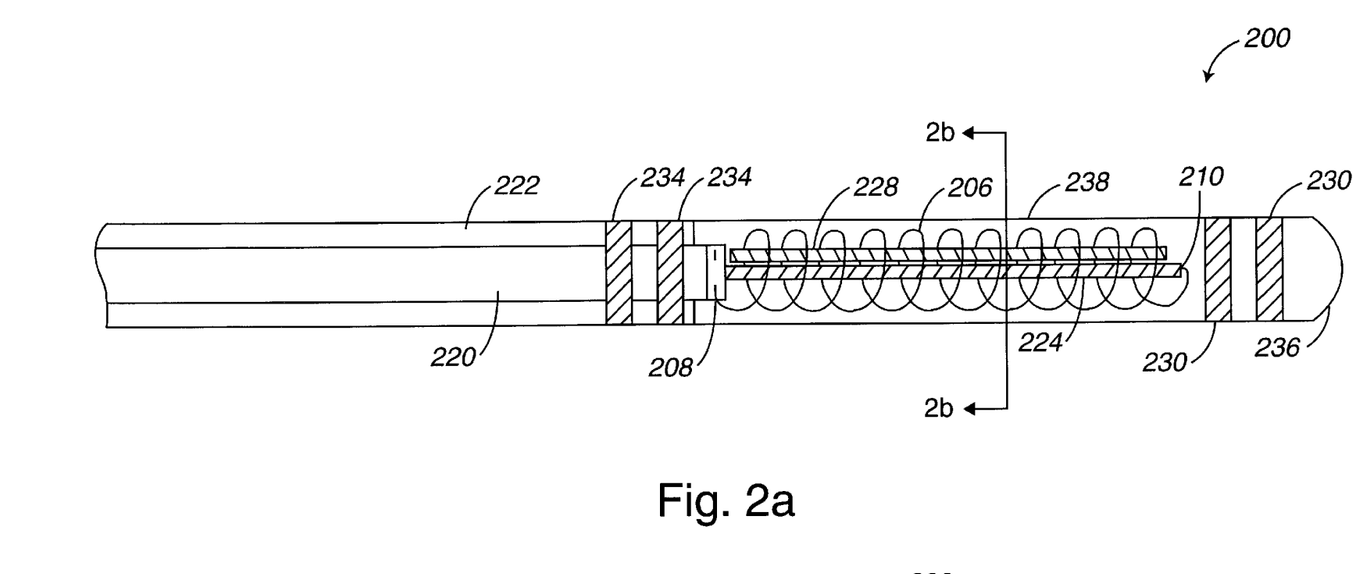
FIG. 2a is a diagrammatic longitudinal cross-sectional view of a conformally positionable ablation catheter tip in accordance with an embodiment of the present invention.
Figure 2B:
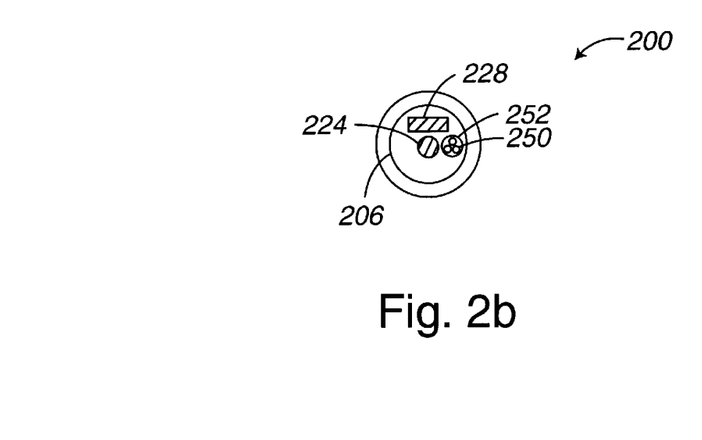

As seen in FIGS. 2a and 2b, a conformally positionable ablation catheter 200 generally includes an antenna 206 with a proximal end 208 and a distal end 210. Proximal end 208 of antenna 206 is grounded to a shield (not shown) of transmission line 220. It should be appreciated that transmission line 220, which is supported within a distal shaft 222, is typically co-axial, and coupled to a power supply, shown in FIG. 7, which is external to catheter 200. Distal end 210 of antenna 206 is attached to center conductor 224 of transmission line 220. Typically, antenna 206 is in the form of a coil, i.e. an antenna coil, which is made from any suitable material, such as spring steel, beryllium copper, or silver-plated copper. The outer diameter of antenna coil 206 will vary to some extent based on the particular application of the catheter. By way of example, a catheter suitable for use in an atrial fibrillation application may have typical coil outer diameters in the range of approximately 0.07 to 0.1 inches. More preferably, the outer diameter of antenna coil 206 may be in the range of approximately 0.08 to 0.09 inches.

As shown, shape memory metal wire 228, is axially located within antenna, or antenna coil, 206. For embodiments in which antenna 206 is not in the form of an antenna coil, shape memory metal wire 228 may be positioned such that longitudinal axes of both antenna 206 and shape memory metal wire 228 are aligned. Shape memory metal wire 228, which is typically a flat wire, may be made from any suitable shape memory metal. The shape of shape memory metal 228 is dependent upon the desired positioning attributes of catheter 200. A shape memory metal is a moldable metal which has a "default," or rest, state. This default state may also be considered to be a neutral state. A shape memory metal is generally a metal which may be shaped when force is applied to the metal. However, when force is removed from a shape memory metal, the metal returns to the default state, which is the original state the metal was in prior to the application of force. The shape memory metal may be any suitable "elastic" metal. By way of example, nickel titanium, copper beryllium, and steel alloys have been observed to work well.

As previously mentioned, the typical shape of shape memory metal wire 228 is a flat shape, e.g. it has a rectangular cross-section where the height of the rectangle is much greater than the width of the rectangle. In general, a flat shape may be considered to be any shape in which the average height of the shape is significantly greater than the average width of the shape. A flat-shaped shape memory metal wire 228 is preferred due to the fact that a flat-shaped shape memory metal wire 228 will have the tendency to bend at one axis, or in one plane. Hence, a flat-shaped shape memory metal wire 228 is easier to control, and, therefore, easier to steer since the flat-shaped shape memory metal wire 228 will not exhibit significant bending in more than one plane. However, although flat cross-sectional shapes are preferred for shape memory metal wire 228, other shapes such as conventional round wires will also work in many applications.

In embodiments which include distal electrodes 230 as illustrated in FIG. 2*a*, sensor conduit 252, shown in FIG. 2*b* (shown in more detail in FIG. 5*b*), which carries sensor wires 250, shown in FIG. 2*b*, is generally located along the longitudinal axis of catheter tip 200. In other words, sensor conduit 252 which carries sensor wires 250 is typically axially located within antenna coil 206. In this case, the term "axially located" refers to sensor conduit 252 being located such that is parallel to the longitudinal axis of antenna coil 206. The sensor wires are connected with distal electrodes 230 which are provided as part of catheter 200 to facilitate positioning of catheter 200 during use. Distal electrodes 230 are used to detect electro-physiological signals from cardiac tissue and, hence, may be used to map the relevant region of the heart prior to or after an ablation procedure. Distal electrodes 230 may also be used to aid in positioning catheter 200 during the ablation procedure. Distal electrodes 230 may be made from a variety of biocompatible materials, which include stainless steel or iridium platinum. Like distal electrodes 230, proximal electrodes 234, which are typically formed from the same biocompatible materials as distal electrodes 230, may also be used for positioning purposes and to map regions of the heart prior to or after an ablation procedure.

The distal tip 236 of catheter 200, which includes the elongated tube portion 238 of catheter 200, i.e. the section of catheter 200 which encapsulates antenna 206, may be formed from a flexible dielectric material. That is, the material which both fills and surrounds antenna coil 206 is typically a flexible dielectric material. Suitable flexible dielectric materials include, but are not limited to, materials such as silicone. One family of silicone products which has been observed to work well is GE Liquid Injection Material (LIM) 6040 through 6070, a silicone family from General Electric in Waterford, N.Y. In general, it is desired for distal tip 236 to be formed from soft, e.g. malleable, materials which are resistant to heat, although in some embodiments, distal tip 236 may be made from Teflon type products.

A flexible tubular member is usually placed or formed over transmission line 220 in a conventional manner. As will be appreciated by those skilled in the art, the flexible tubular member may be made from any suitable material including, but not limited to, medical grade polyolefins, fluoropolymers, or polyvinylidene fluoride. By way of example, PEBAX resins from Autochem of Germany have been used with success.

In general, the dimensions of catheter 200 are dependent upon the requirements of a particular application for the catheter. However, a catheter tip diameter, e.g. the diameter of elongated tube portion 238, in the range of approximately 7 to 9 French, or approximately 0.092 to 0.141 inches, has been observed to work well for most cardiac applications. It is generally desired that the catheter tip diameter exceed the diameter of the antenna coil, in order to properly encapsulate the antenna coil. By way of example, excess catheter tip diameters in the range of approximately 0.005 to 0.015 inches, as for example approximately 0.01 inches, more than the diameter of the antenna coil work well. A catheter tip length in the range of approximately 0.2 to 2.5 inches is preferable. More preferably, a catheter tip length is in the range of approximately 1.2 to 2 inches. The catheter tip length varies as a result of any number of factors which include, but are not limited to, the particular requirements of the application and the size of a patient's heart.

One method for using the described catheter in an ablation procedure will now be described. The catheter may be fed through the femoral artery or any other suitable vessel and into the appropriate region of the heart. By way of example, to treat atrial fibrillation, the catheter tip, which is the distal tip of the catheter, is typically fed into the appropriate atrial chamber. The conformally positionable ablation catheter as described with respect to FIG. 2*a* may be passively steered. That is, once the tip of the catheter is positioned in proximity of a desired position in a chamber of the heart using standard steering methods which are well known in the art, the catheter tip may be rotated such that it may reach the desired position. Specifically, as previously described, a flat shape memory metal wire may bend significantly only along one axis, or in one plane. As such, the catheter may have to be rotated such that the "bending-axis" is properly oriented to facilitate the conforming of the catheter tip to the wall of the heart chamber. Once the distal portion of the catheter tip engages the wall of the heart chamber, a rotation of the catheter tip and the application of force will generally enable the catheter tip to conform to the wall of the heart chamber. It should be appreciated that any suitable method may be used to apply force to the catheter tip and, hence, the shape memory metal within the catheter tip. One method which may be used to apply force to the catheter tip may entail applying a force by "pushing" or pressing the catheter tip further against the wall of the heart chamber. The shape memory metal conforms, along with the catheter tip, to the wall of the heart chamber.

With the catheter properly positioned, the electrodes, or any suitable sensor, can detect electrical signals or, more specifically, electro-physiological signals, in the adjacent regions of the heart. If necessary, the catheter may be further inserted, and or withdrawn to facilitate a mapping of the region of interest. Typically, mapping will indicate the location at which relevant electro-physiological signals, or cardiac signals, as for example EKGs, are strongest. This, in turn, will permit a physician to determine the appropriate ablation position. The catheter is then positioned as necessary to locate the antenna properly for the ablating procedure. After the antenna is properly positioned, microwave energy is applied to the co-axial transmission line to facilitate the ablation. During the ablation procedure, as well as after the operation is completed, the electrodes may be used to monitor the ablation process as well as the results. A suitable microwave generator will be described below with reference to FIG. 7.

When it is desired for the conformally positionable catheter tip to be removed from the wall of the heart chamber or repositioned within the heart chamber, the force pressing the catheter against the heart wall may be at least partially released to enable the catheter to be moved. At least partially releasing the force pressing the catheter against the heart wall also releases at least some of the force on the shape memory metal within the catheter tip. An almost complete removal of force from the catheter tip will enable the shape memory metal and, hence, the catheter tip to return to their original, default shapes. That is, the shape memory metal will return to the state it was in prior to the application of force.

Figure 3:
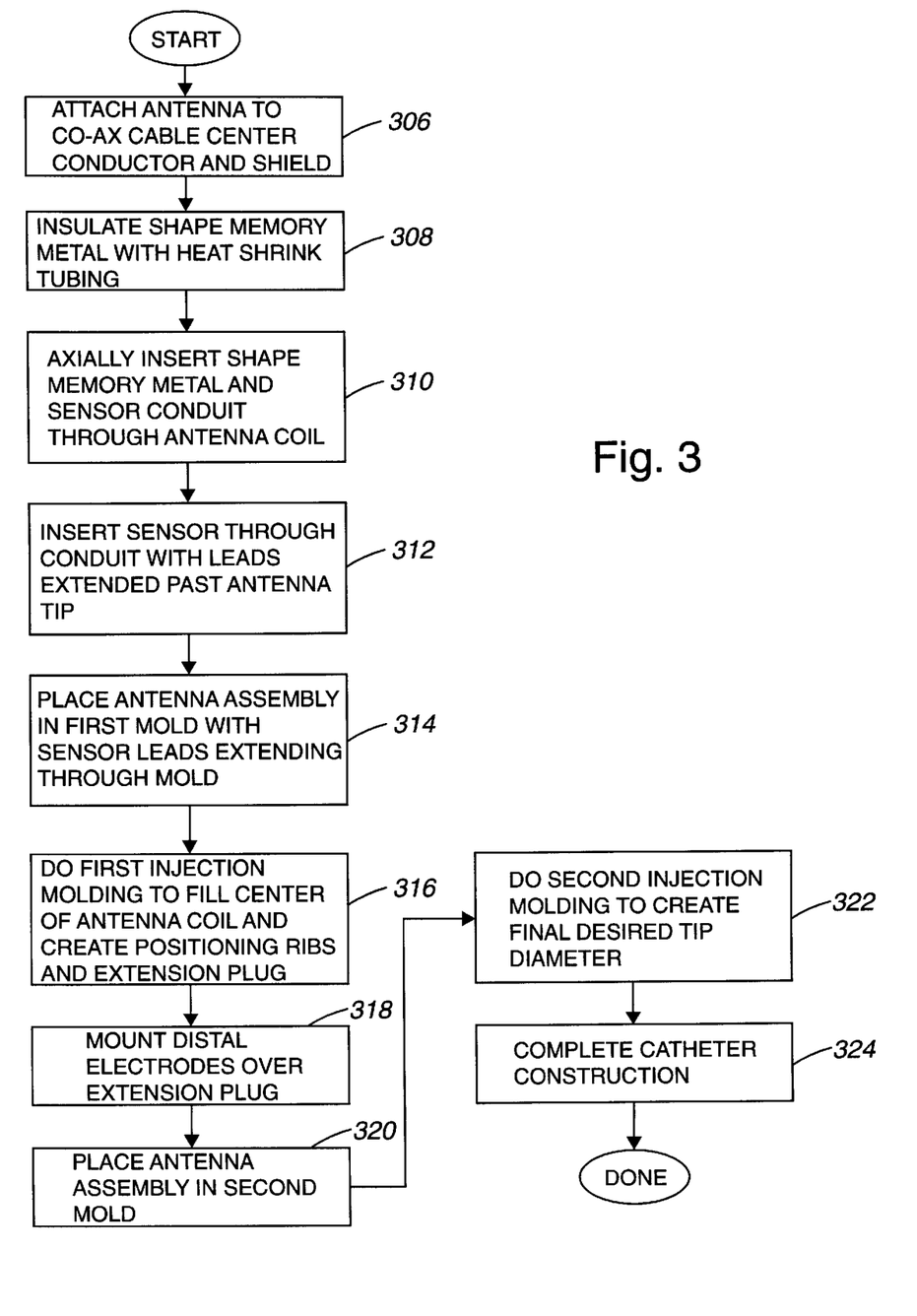
FIG. 3 is a flow chart which illustrates steps in a process for manufacturing a conformally positionable ablation catheter in accordance with an embodiment of the present invention.

Referring next to FIG. 3, a process for manufacturing a conformally positionable ablation catheter in accordance with one embodiment of the present invention will be described. Initially in step 306, an antenna is attached to the center conductor and the shield of a co-axial cable. It should be appreciated that the co-axial cable is a co-axial transmission line. The distal end of the antenna is connected with the center conductor, while the proximal end of the antenna is grounded to the shield. The antenna may be formed from any suitable material, as for example silver plated copper wire or beryllium copper wire. As will be appreciated by those skilled in the art, the antenna is generally an antenna coil. In the illustrated embodiments, the antenna coil is helically wound.

A piece of shape memory metal is insulated with heat shrink tubing in step 308 in order to prevent the shape memory metal from shorting against the antenna. The heat shrink tubing is heated and shrunk so that it tightly covers the shape memory metal. As previously described, the shape memory metal may be any suitable "elastic" metal, as for example nickel titanium, a chromium alloy, or a molybdenum alloy. Further, although the shape memory metal is typically elongated with a flat, e.g. rectangular, cross-section, it should be appreciated that the shape memory may take on any number of shapes. By way of example, the shape memory metal may have a round cross-section. A shape memory metal with a flat cross-section is generally preferred, as such a shape memory metal has the tendency to bend in only one direction, i.e. along a single axis, whereas a shape memory metal with a round cross-section may bend in any number of directions.

In step 310, the insulated shape memory metal and a sensor conduit are axially inserted through the antenna coil. That is, the shape memory metal and the sensor conduit are inserted through the antenna coil along the longitudinal axis of the antenna coil. The sensor conduit, which is designed to house sensor leads, may be a polyimide tube. After the shape memory metal and the sensor conduit are properly inserted through the antenna coil, sensor leads are inserted through the sensor conduit such that the leads extend past the tip of the antenna coil in step 312. The sensor leads extend past the tip of the antenna coil to facilitate the attachment of the sensor leads to sensors, which are typically electrodes.

The antenna coil, the sensor conduit with the sensor leads, and the shape memory metal, which together comprise an antenna assembly, are placed in a first mold in step 314. The first mold is generally used to concentrically position the sensor conduit and shape memory metal relative to the antenna coil and to facilitate the creation of positioning ribs along the perimeter of the antenna coil. The first mold, which will be described in more detail below with reference to FIGS. 4a and 4b, has a cavity 404 which supports the antenna coil 412 and, therefore, enables the antenna coil 412 to be filled with a dielectric material. The cavity 404 has a diameter which is substantially equal to the diameter of the antenna coil 412, and is therefore able to support the antenna coil 412 while it is within the cavity 404. The antenna assembly 410 is positioned in the first mold 400 such that the sensor leads 414 extend through the first mold 400. In step 316, a first injection molding operation is performed to fill the center of the antenna coil 412 and to create positioning ribs and an extension plug around the antenna coil 412. That is, a first injection molding operation is essentially used to partially encapsulate and fill the antenna assembly 410. The partially encapsulated antenna assembly 410 will be described below with respect to FIGS. 5a and 5b. Typically, the positioning ribs 510 are formed along the perimeter of the antenna assembly 406 such that the distance from the edge of one positioning rib, as for example edge 512a positioning rib 510a, to the edge of a directly opposing positioning rib, as for example edge 512c of positioning rib 510c, is equal to the desired, final outer diameter of the completed antenna assembly.

The first injection molding operation may be performed using any suitable pliant material including, but not limited to, silicone. In addition to being flexible when it is cured, silicone is not self-heating, which is a desirable characteristic for a material used in the fabrication of a catheter. As previously described, one type of silicone which has been observed to work well is GE Liquid Injection Material (LIM) 6040, a silicone from General Electric in Waterford, N.Y.

After the first injection molding operation is completed, the distal electrodes 538, if any, are mounted over the extension plug 520 in step 318. A distal electrode 538 is generally a band. However, in the described embodiment, the distal electrodes 538 may be annular bands which may be cut into segments after they are mounted, i.e. installed, or the distal electrodes 538 may be independent segments that form associated bands only after installation. The distal electrodes 538 are connected to the specific sensor, or electrode, leads 537 with which they are associated, thereby forming an electrode ring assembly having the desired number of electrode wires, such as a pair of electrode wires, which may then be slid over the antenna assembly and positioned in its desired location. In some embodiments, heat shrink tubing is then heated and shrunk over the distal electrodes 538 such that the heat shrink tubing tightly covers the electrodes 538 and seals electrode wire holes through which the sensor wires 537 pass. In other embodiments, the distal electrodes 538 may be covered with ultraviolet (UV) curable epoxy which is then cured to set the electrodes 538.

The electrodes 538 are provided to facilitate positioning of the catheter 502 during use. The electrodes 538 are used to detect electro-physiological signals from cardiac tissue and may therefore be used to map the relevant region of the heart prior to or after an ablation procedure. The electrodes 538 may also be used to aid in positioning the catheter 502 for use and to monitor the patient's condition during the ablation process. Although electrodes 538 may be made from a variety of different biocompatible materials, electrodes 538 are typically made of either stainless steel or iridium platinum.

In step 320, the antenna assembly, which, at this point in the process, is partially molded over, is placed in a second mold which is used to set the final outer diameter of the tip of the completed antenna assembly. As described above, the distance from the edge of one positioning rib 510 to the edge of a directly opposing positioning rib 510 is typically equal to desired outer diameter of the completed antenna assembly. The second mold, besides being used to set the final outer diameter of the completed antenna assembly, is used to eliminate any bubbles which may have been formed in the catheter as a result of the first injection molding process. The second mold will be discussed in more detail below with reference to FIG. 6.

A second injection molding operation is performed in step 322 to create the final desired diameter of the antenna assembly, or more specifically, the final desired tip diameter of the antenna assembly. The same material which was used in the first injection molding operation is generally also used for the second injection molding operation, though any suitable material may be used. The antenna assembly with the final desired tip diameter may be considered to be a conformal positioning assembly.

After the second injection molding operation is completed, the remaining steps associated with the catheter construction process are performed in step 324. These steps include, but are not limited to, inserting the co-axial cable into a distal shaft, or a flexible tubular member, in a conventional manner. The conventional manner involves binding the antenna assembly to the distal end of the flexible tubular member and attaching the handle to the proximal end of the flexible member. As will be appreciated by those skilled in the art, the flexible tubular member may be made from any suitable material including, but not limited to, medical grade polyolefins, fluoropolymers, or polyvinylidene fluoride. By way of example, PEBAX resins from Autochem of Germany have been used with success in molding the body of the catheter. Stiffening wires, steering wires, additional sensor wires, etc., may all be included in the final assembly as required by a particular design. After the final assembly is completed, the process of manufacturing a conformally positionable catheter is completed.

Figure 4A:
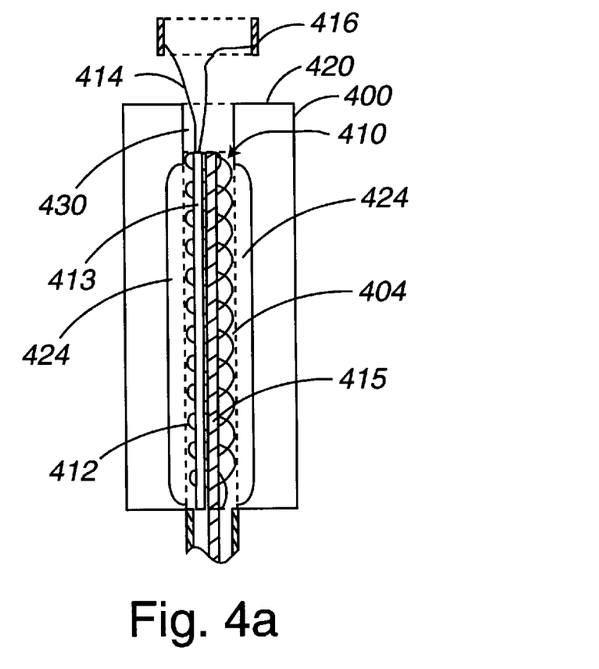
FIG. 4a is a diagrammatic cross-sectional view of an initial mold used to position an antenna assembly during a first molding operation in accordance with an embodiment of the present invention.
Figure 4B:
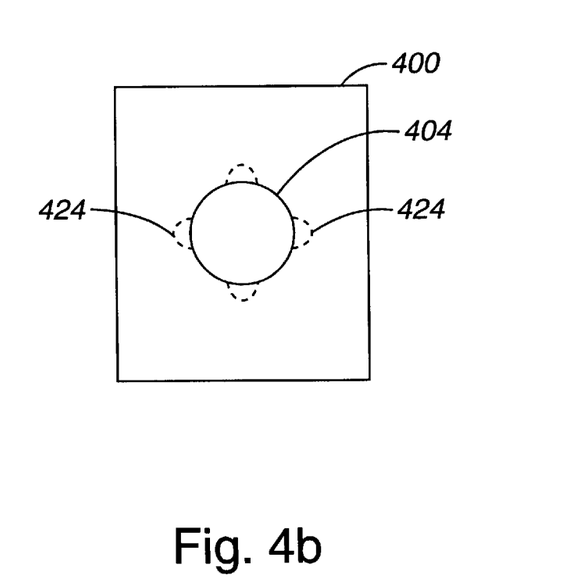
FIG. 4b is a diagrammatic top view of the mold as shown in FIG. 4b.

Referring next to FIGS. 4a and 4b, a mold used to position an antenna assembly will be described in accordance with an embodiment of the present invention. In other words, the mold used in the first injection molding operation as mentioned above with respect to FIG. 3 will be described. FIG. 4a is a diagrammatic cross-sectional view of a mold used to position an antenna assembly, i.e. an antenna, a shape memory wire, and a sensor conduit which houses sensor wires. FIG. 4b is a diagrammatic top view of mold 400 as shown in FIG. 4a. Mold 400, which may be made from any suitable material, has a main cavity 404 in which an antenna assembly 410 is situated. Main cavity 404, as shown, comes into contact with rib cavities 424 which are used to form positioning ribs around antenna assembly 410. Main cavity 404 is further sized such that edges of main cavity, as for example edges 411, come into contact with antenna assembly 410 and, more specifically, an antenna coil 412. That is, the diameter of main cavity 404 is substantially the same as the diameter of antenna coil 412. The shape, or an axial cross-section, of main cavity 404 is dependent upon the desired shape, i.e. axial cross-section, of the molded over antenna assembly (not shown). Typically, the shape of main cavity 404 is either circular (as shown) or oval. However, it should be understood that the shape may be widely varied depending upon the requirements of a particular antenna assembly.

Although only antenna coil 412 and a sensor conduit 413 with sensor wires 414 have been shown to comprise antenna assembly 410, it should be appreciated that antenna assembly 410 also includes a shape memory wire (not shown) and a transmission line 415. However, purely for ease of illustration, antenna assembly 410 has been generically represented, and the shape memory wire has not been shown in FIG. 4a. Sensor wires 414, which are attached to an electrode ring 416, extend past the top edge 420 of mold 400.

In order to align the components of antenna assembly 410, i.e. antenna coil 412, sensor conduit 413 with sensor wires 414, the shape memory metal (not shown), the transmission line 415, as required for a particular catheter, mechanisms external to mold 400 may be used to hold and otherwise position antenna assembly 410. However, in general, mold 400 is capable of supporting antenna coil 412 for positioning purposes. The shape memory metal and the sensor conduit may suitably be aligned by allowing the shape memory metal and sensor conduit 413 to be held against transmission line 415 within antenna assembly 410. Once the components of antenna assembly 410 are suitably aligned, an injection molding operation which uses any suitable material, as for example silicone as described above with respect to FIG. 3, is implemented to fill the center of antenna coil 412 as well as to create positioning ribs and an extension plug around antenna assembly 410. The positioning ribs are formed using rib cavities 424, while the extension plug is generally formed on antenna assembly 410 near top edge 420 of mold 400 in the top portion 430 of main cavity 404. The extension plug is formed to provide a surface over which electrode ring 416 may be mounted. The diameter of the extension plug after the first molding operation will generally be the equal to the diameter of main cavity 404. In some embodiments, mold 400 may be comprised of at least two distinct pieces which may be interconnected during the molding process, and separated after the molding process in order to remove antenna assembly 410 from mold 400.

In the embodiment as shown, main cavity 404 extends approximately the length of mold 400, while rib cavities 424 extend less than the length of mold 400. As will be appreciated by those skilled in the art, the relative depths, or more generally, dimensions of main cavity 400 and rib cavities 424 may vary greatly depending upon the requirements of a specific antenna assembly.

Figure 5A:
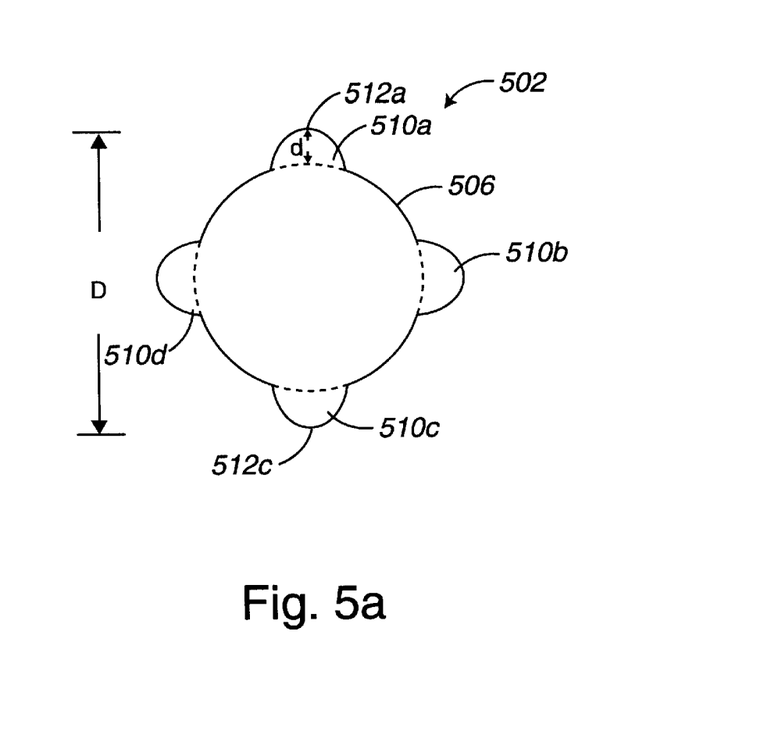
FIG. 5a is a diagrammatic cross-sectional axial view of a conformally positionable antenna assembly after a first molding process in accordance with an embodiment of the present invention.
Figure 6:
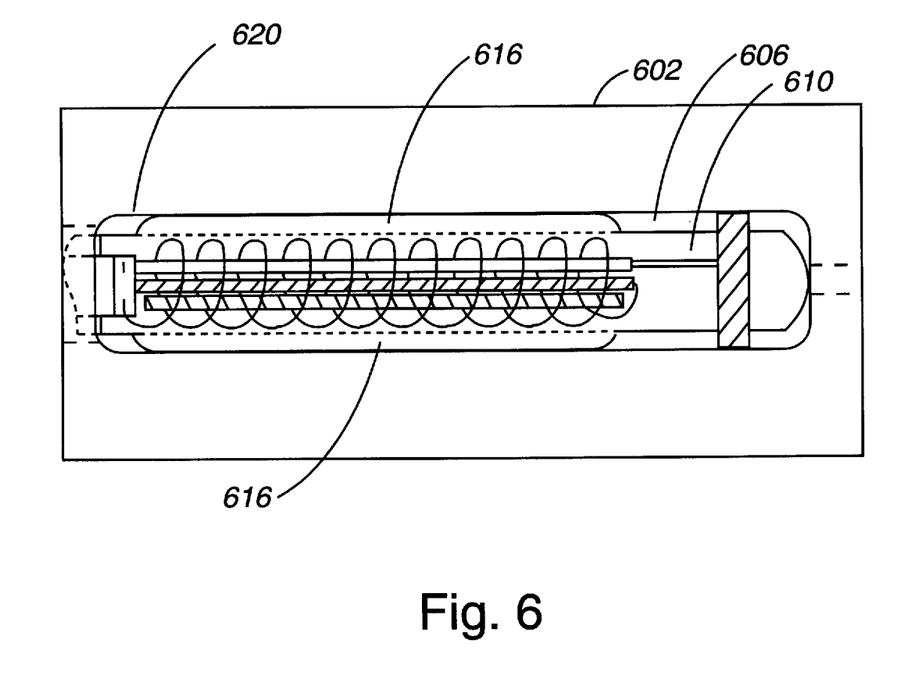
FIG. 6 is a diagrammatic top view of a second mold used to create a desired tip diameter for an ablation catheter in accordance with an embodiment of the present invention.

Referring next to FIG. 5a, a diagrammatic cross-sectional axial view of a partially molded conformally positionable antenna assembly after a first molding process in accordance with an embodiment of the present invention will be described. It should be appreciated that the cross-sectional view is shown without an antenna coil, a sensor conduit, a shape memory wire and transmission line for illustrative purposes. That is, only the "outline" of conformally positionable antenna assembly 502 is shown for ease of illustration. Further, the cross-section of antenna assembly 502 that is shown is away from the extension plug formed at the distal end of antenna assembly 502. The "main body" 506 of antenna assembly, which is comprised of any suitable malleable material, as for example silicone as described above, encapsulates the antenna coil, sensor conduit, shape memory wire, etc. Although main body 506 may have any cross-sectional shape, in the embodiment as shown, main body 506 has a circular cross-section. Positioning ribs 510, which are used to position antenna assembly 502 within a second mold used to complete the antenna tip assembly as will be described below with reference to FIG. 6, are formed along the perimeter of main body 506, and are made of the same material as main body 506. The tip-to-tip distance D from the tip of a first positioning rib, as for example positioning rib 510a with tip 512a, to the tip of a second positioning rib which is directly opposite the first positioning rib, as for example positioning rib 510c with tip 512c, is generally approximately equal to the desired diameter of the completed antenna tip (not shown).

Positioning ribs 510 may take on any suitable cross-section. However, positioning ribs 510 which have curved, e.g. semi-circular, axial cross-sections are preferable due to the fact that the final antenna tip assembly has a round cross-section. That is, the completed catheter assembly has a round cross-section. Hence, positioning ribs 510 have curved cross-sections for ease of manufacturability. As will be appreciated by those skilled in the art, utilizing positioning ribs 510 with axial cross-sections which are rectangular, for example, would have the tendency to require an end mill to "shave" the edges of the rectangle in order to achieve the desired diameter of the completed antenna tip.

Although any number and orientation of positioning ribs 510 may be used, in the described embodiment, four positioning ribs 510 which are symmetrical about the perimeter of main body 506 are shown. This number and orientation of positioning ribs 510 have been shown to be effective in securely positioning antenna assembly 502 within the aforementioned second mold. Each positioning rib, as for example positioning rib 510a, has a "height," i.e. tip-to-base dimension, d in the range of approximately 0.005 to 0.01 inches, as for example approximately 0.007 inches.

Figure 5B:
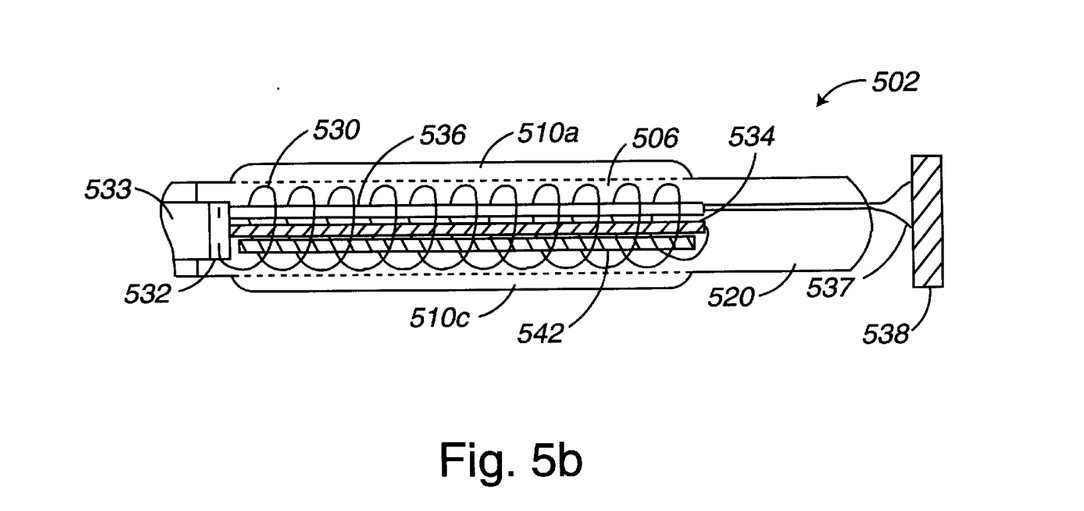

FIG. 5b a diagrammatic longitudinal side view of the partially molded conformally positionable antenna assembly of FIG. 5a. Antenna assembly 502 includes main body 506, an extension plug 520 formed at the distal end of antenna assembly 502, and positioning ribs 512. It should be appreciated that only two positioning ribs, i.e. positioning ribs 510a and 510c, have been shown for ease of illustration. Antenna assembly 530 includes, as previously described, an antenna coil 530, a sensor conduit 536, and a shape memory metal 542. Antenna coil 530 is coupled at a proximal end to the shield 532 of co-axial cable, or transmission line, 533 which effectively serves to ground antenna coil 530. At a distal end, antenna coil 530 is coupled to the center conductor 534 of co-axial cable 533. Sensor conduit 536 houses sensor wires 537 which are coupled to an electrode 538. Electrode 538, as shown, has not yet been mounted over extension plug 520. Although only one electrode 538 has been shown, it should be appreciated that the number of electrodes coupled to sensor wires 537, as well as the number of sensor wires 537, is dependent upon the requirements of a particular catheter.

Referring next to FIG. 6, the second mold used in forming a conformally positionable catheter will be described. FIG. 6 is a diagrammatic top view of the mold used to create a desired tip diameter for a catheter in accordance with an embodiment of the present invention. Mold 602 is used primarily to create the desired tip diameter for a conformally positionable catheter. Mold 602 includes cavity 606 which holds the antenna assembly 610, as previously described with respect to FIGS. 5a and 5b, after the distal electrode of the antenna assembly has been properly mounted over the extension plug. Antenna assembly 610 will fit into cavity 606, prior to the second injection molding process, substantially as shown. As the tip-to-tip distance between positioning ribs 616 is approximately equal to the final diameter of the catheter tip formed using mold 602, positioning ribs 616 is shown to be flush with the edges 620 of cavity 606.

Figure 7:
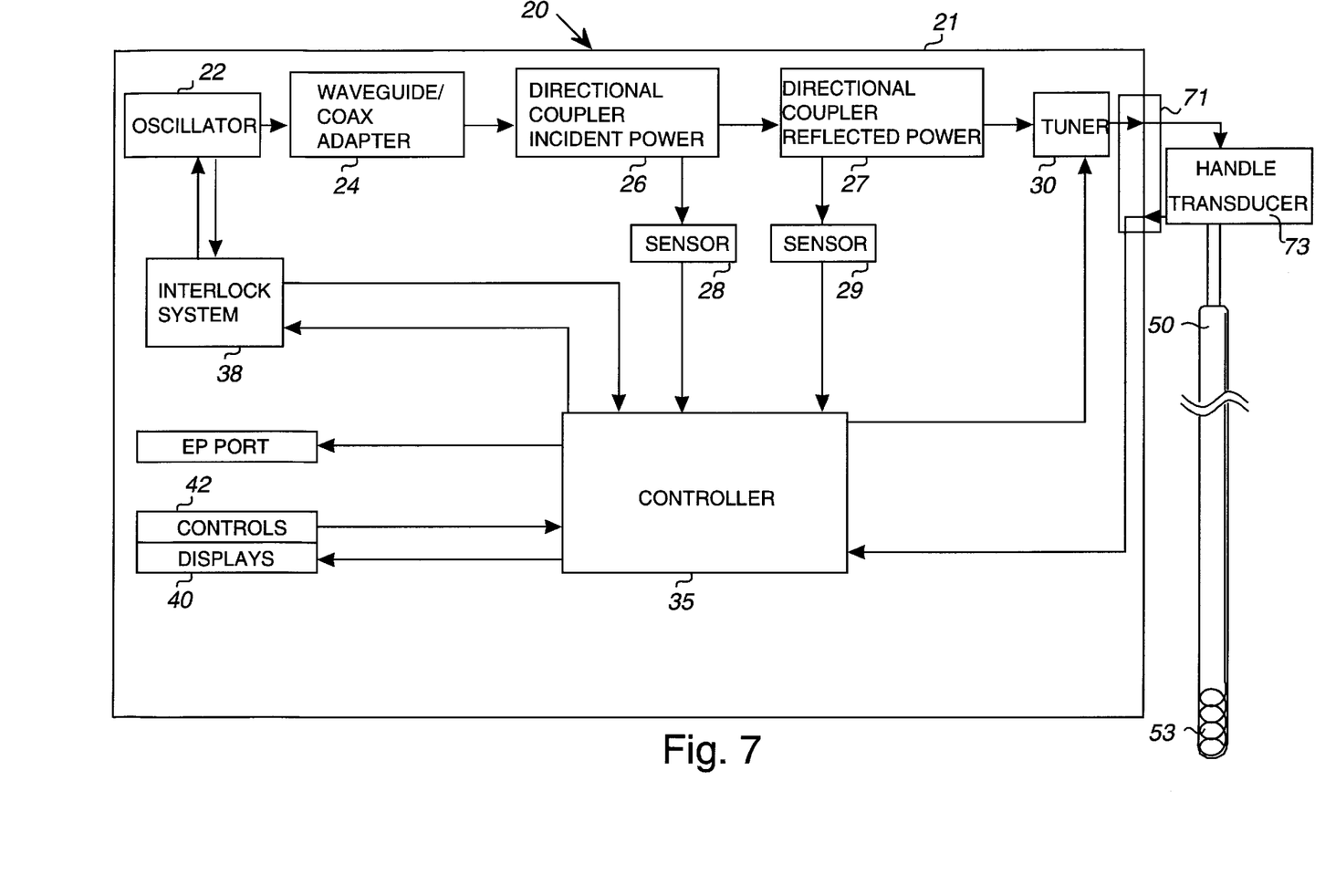
FIG. 7 is a diagrammatic illustration of a microwave ablation catheter system in accordance with an embodiment of the present invention.

A suitable microwave generator which may be used with the conformally positionable catheter will now be described. FIG. 7 is a diagrammatic illustration of a microwave ablation catheter system in accordance with an embodiment of the present invention. An ablation catheter system 10 generally includes a power supply 20 which is designed to generate controlled electromagnetic energy, a catheter 50 which is designed for insertion into a vessel (such as a coronary vessel) in the body of a patient and a connector 71 for coupling the power supply 20 to the catheter 50. As previously described with respect to FIG. 2a, the catheter typically includes a flexible outer tubing, a co-axial microwave transmission line that extends through the flexible tubing, and an antenna 56 coupled to the distal end of the co-axial transmission line. The connector couples transmission line 53 to external power supply 20. A handle 73 may be provided for use by the surgeon to facilitate steering and potentially other control functions. Additionally, catheter 50 may include a variety of sensors for monitoring the patient during insertion, positioning and/or use of the catheter. By way of example, such sensors may include a plurality of mapping electrodes 230, as shown in FIG. 2a, and one or more thermocouple wires (not shown). The co-axial microwave transmission line 53 includes a center conductor, a shield, and a dielectric material disposed between the center conductor and shield.

Although only a few embodiments of the present invention have been described, it should be understood that the present invention may be embodied in many other specific forms without departing from the spirit or scope of the present invention. By way of example, although the invention has been described in terms of a conformally positionable microwave ablation catheter for cardiac applications, it should be appreciated that the described conformally positionable microwave ablation catheter could be used for a wide variety of non-cardiac ablation applications as well.

Further, although two molding operations have been described, it should be apparent that the use of a single molding operation to form a conformally positionable microwave ablation catheter tip does not represent a departure from the spirit or the scope of the present invention. By way of example, a single molding operation may be used both to align the antenna assembly and to create the desired tip diameter of the ablation catheter tip. Therefore, the present examples are to be considered as illustrative and not restrictive, and the invention is not to be limited to the details given herein, but may be modified within the scope of the appended claims.

We claim:

1. An ablation catheter comprising:
    an elongated flexible tubular member adapted to be inserted into a vessel in the body of a patient, the flexible tubular member including a distal portion and a proximal portion;
    a transmission line disposed within the tubular member, the transmission line having proximal and distal ends, wherein the proximal end of the transmission line is suitable for connection to an electromagnetic energy source;
    a transducer coupled to the transmission line for generating an electric field sufficiently strong to cause tissue ablation; and
    a shape memory wire positioned at a distal portion of the catheter adjacent the transducer, the shape memory wire being arranged to deform when the distal portion of the catheter deforms.

2. A catheter as recited in claim 1 wherein the shape memory wire is formed from a material selected from the group consisting of chromium, molybdenum, copper beryllium, steel, and nickel titanium.

3. A catheter as recited in claim 1 wherein the shape memory wire is flat.

4. A catheter as recited in claim 1 wherein the shape memory wire has a circular cross section.

5. A catheter as recited in claim 1 further comprising a distal tip portion of the flexible tubular member, wherein the distal tip portion is formed from a silicone material that encapsulates the transducer and the shape memory wire.

6. A catheter as recited in claim 1 further comprising a plurality of electrode bands that are longitudinally spaced along the flexible tubular member, each electrode band including a plurality of electrically isolated electrodes.

7. An ablation catheter comprising:

a elongated flexible tubular member adapted to be inserted into a vessel in the body of a patient, the flexible tubular member including a distal portion and a proximal portion;

a transmission line disposed within the tubular member, the transmission line being a co-axial cable having proximal and distal ends, wherein the proximal end of the transmission line is suitable for connection to an electromagnetic energy source;

a transducer coupled to the transmission line for generating an electric field sufficiently strong to cause tissue ablation, wherein the transducer is a helical antenna coil that is adapted to radiate electromagnetic energy in the microwave frequency range; and a shape memory wire positioned at a distal portion of the catheter adjacent the transducer, wherein the shape memory wire is further positioned within the antenna coil.

8. A catheter as recited in claim 7 wherein the shape memory wire is flat.

9. A catheter as recited in claim 7 wherein the shape memory wire has a circular cross section.

10. A catheter as recited in claim 7 further comprising a distal tip portion of the flexible tubular member, wherein the distal tip portion is formed from a silicone material that encapsulates the transducer and the shape memory wire.

11. A catheter as recited in claim 7 further comprising a multiplicity of electrode bands that are longitudinally spaced along the flexible tubular member, each electrode band including at least one electrically isolated electrode.

12. A catheter as recited in claim 7 wherein the shape memory wire is formed from a material selected from the group consisting of chromium, molybdenum, nickel titanium, copper beryllium, and steel.

13. A microwave ablation catheter comprising:

an elongated flexible tubular member adapted to be inserted into a vessel in the body of a patient, the flexible tubular member including a distal portion and a proximal portion;

a co-axial cable disposed within the tubular member, the co-axial cable having proximal and distal ends, wherein the proximal end of the co-axial cable is suitable for connection to an electromagnetic energy source;

a helical antenna coil coupled to the co-axial cable for generating an electric field sufficiently strong to cause tissue ablation; and a shape memory wire positioned within the antenna coil.

14. A microwave ablation catheter as recited in claim 13 wherein:

the shape memory wire is flat; and the distal portion of the flexible tubular member is formed from a silicone material that encapsulates the helical antenna coil and the shape memory wire.

15. A microwave ablation catheter as recited in claim 14 wherein:

the helical antenna coil has an outer diameter in the range of approximately 0.07 to 0.1 inches; and the helical antenna coil has a length in the range of approximately 0.2 to 2.5 inches.

16. A microwave ablation catheter as recited in claim 15 wherein the microwave ablation catheter is an atrial fibrillation catheter, the atrial fibrillation catheter being arranged to ablate arrhythmia circuits associated with the heart of the patient.

17. A microwave ablation catheter as recited in claim 16 wherein the shape memory wire is formed from a material selected from the group consisting of copper beryllium, steel alloys, and nickel titanium.

18. A microwave ablation catheter as recited in claim 17 further comprising:

a plurality of electrode bands that are longitudinally spaced along the flexible tubular member, each electrode band including a plurality of electrically isolated electrodes; and a sensor conduit positioned within the antenna coil, the sensor conduit including sensor wires, wherein the sensor wires are coupled to the electrode bands.

* * * * *